(12) United States Patent
Ohmura et al.

(10) Patent No.: US 8,567,391 B2
(45) Date of Patent: Oct. 29, 2013

(54) HEAT AND MOISTURE EXCHANGER, HEAT AND MOISTURE EXCHANGING DEVICE, AND MASK

(75) Inventors: Akito Ohmura, Tokyo (JP); Kunihisa Eguchi, Tokyo (JP); Tetsuya Miyaji, Tokyo (JP); Katsuyoshi Goto, Tokyo (JP)

(73) Assignee: Furrex Co., Ltd., Tokyo (JP)

( * ) Notice: Subject to any disclaimer, the term of this patent is extended or adjusted under 35 U.S.C. 154(b) by 833 days.

(21) Appl. No.: 12/421,387

(22) Filed: Apr. 9, 2009

(65) Prior Publication Data

US 2009/0301478 A1 Dec. 10, 2009

Related U.S. Application Data

(63) Continuation-in-part of application No. PCT/JP2007/070208, filed on Oct. 10, 2007, and a continuation-in-part of application No. PCT/JP2009/001047, filed on Mar. 9, 2009.

(60) Provisional application No. 60/850,698, filed on Oct. 10, 2006, provisional application No. 61/043,474, filed on Apr. 9, 2008, provisional application No. 61/105,929, filed on Oct. 16, 2008.

(51) Int. Cl.
*A62B 7/10* (2006.01)

(52) U.S. Cl.
USPC ............................... 128/201.13; 128/204.17

(58) Field of Classification Search
USPC ............. 128/201.13, 204.17, 205.27, 205.29, 128/206.12, 206.13, 206.19
See application file for complete search history.

(56) References Cited

U.S. PATENT DOCUMENTS 3,333,585 A * 8/1967 Barghini et al. .......... 128/201.13
4,883,052 A * 11/1989 Weiss et al. .............. 128/205.27
(Continued)

FOREIGN PATENT DOCUMENTS

EP 0265163 A2 4/1988
GB 2267661 A 12/1993
(Continued)

OTHER PUBLICATIONS

Turnbull, D. et al. Performance of breathing filters under wet conditions: a laboratory evaluation. Brit. J. of Anaesth. 2005. 94(5), 675-682.*

(Continued)

*Primary Examiner* — Lynne Anderson
*Assistant Examiner* — Kathryn E Ditmer
(74) *Attorney, Agent, or Firm* — Harness, Dickey & Pierce, PLC

(57) ABSTRACT

A heat and moisture exchanger configured to be located between a respiratory system of a patient and an anesthesia circuit connected to an anesthesia apparatus, or a respiratory circuit connected to a respirator for maintaining a temperature and humidity of an aspired gas required to a patient under anesthesia or artificial respiration comprises a heat storage carrier material, and a moisture absorption and release material added to the heat storage carrier material. In the heat and moisture exchanger, at least one of density of the heat storage carrier material, number of cells of the heat storage carrier material, and an added amount of the moisture absorption and release material in the heat storage carrier material is set to decrease from the patient side to the side of the anesthesia apparatus or the respirator, along a flow direction of a respiratory gas in the heat storage carrier material.

18 Claims, 12 Drawing Sheets

(56) References Cited

U.S. PATENT DOCUMENTS

| | | |
|---|---|---|
| 5,284,160 A | 2/1994 | Dryden |
| 5,706,802 A | 1/1998 | McCormick |
| 5,992,413 A | 11/1999 | Martin, Jr. et al. |
| 6,105,576 A * | 8/2000 | Clawson et al. ......... 128/205.12 |
| 6,196,221 B1 | 3/2001 | McCormick |
| 7,069,928 B1 | 7/2006 | Waldo, Jr. et al. |

FOREIGN PATENT DOCUMENTS

| | | |
|---|---|---|
| GB | 2267840 A | 12/1993 |
| JP | 62-119954 | 7/1987 |
| JP | 06-063141 | 3/1994 |
| JP | 2000-225205 | 8/2000 |
| JP | 2006-136461 | 6/2006 |
| JP | 2006136461 A * | 6/2006 |
| WO | WO-99/33523 A1 | 7/1999 |

OTHER PUBLICATIONS

"Heat and Moisture Exchanger (Filter)—Element Device and Humidification-", Japanese Journal of Respiratory Care Medicine 21-1, pp. 1-7, edited by K. Ishiii; Abstract on p. 2.

* cited by examiner

HEAT AND MOISTURE EXCHANGER, HEAT AND MOISTURE EXCHANGING DEVICE, AND MASK

CROSS-REFERENCE TO RELATED APPLICATIONS

The present application is a continuation-in-part of International Application PCT/JP2007/070208 designating the U.S., with an international filing date of Oct. 10, 2007, claiming a priority from U.S. provisional patent application No. 60/850,698 filed on Oct. 10, 2006, the contents of which are herein incorporated by reference, and of International Application PCT/JP2009/070208 designating the U.S., with an international filing date of Mar. 9, 2009, claiming priorities from U.S. provisional patent applications No. 61/043,474 filed on Apr. 9, 2008 and No. 61/105,929 filed on Oct. 16, 2008, the contents of which are herein incorporated by reference.

BACKGROUND ART

1. Technical Field

The present invention relates to a respiratory heat and moisture exchanger, heat and moisture exchanging device, and mask, and more particularly, to a respiratory heat and moisture exchanger, heat and moisture exchanging device, and mask for appropriately adjusting the temperature and moisture of a gas such as air for a patient to inhale.

2. Related Art

Two kinds of devices have been usually employed to humidify and warm an aspired (inhaled) dry gas when using an anesthesia device, a respirator, or other devices.

One is a heat and moisture exchanging device (HME, called an "artificial nose") of a passive type, and the other is a warmer/humidifier of an active type operated with a heat source.

The passive HMEs are further categorized into three types:
  a type having hydrophilic material charged with hygroscopic substance;
  a type having hydrophobic material charged with hygroscopic substance; and
  a type having a combination of hydrophobic and hydrophilic layers.

For example, Japanese Patent Application Laid-open Publication No. H06-63141 discloses the third type HME. In the reference, entitled "Heat and Moisture Exchanger (Filter)—Element Device and Humidification—", Japanese Journal of Respiratory Care Medicine 21-1, P. 1-7, edited by K. Ishii, described in detail are the HMEs.

For all types, it is understood that some amount of water vapor in the expiratory (exhaled) gas is condensed at a dew point in spaces minutely formed in an element of the HMEs, and meanwhile, the aspiratory gas serves to evaporate the condensed water for humidification. In case of warming of aspiratory gas, it is predicted that there will occur cyclic and local phenomena of thermal storage or heat storage.

At present, the passive types are prevailing because of the advantages of being compact, lightweight, and low-cost while minimizing the risk of medical accidents, mainly arising from usage of a heat source and lack of humidifying due to failure in supplying additional water in the active type. However, it is a fact that as far as performance in warming and humidifying is concerned, the passive types are generally inferior when compared to the active ones.

The above conventional HMEs, however, have the following problems. One problem is that an airway of a patient tends to dry because of poor warming and humidifying capability and a fatal complication may be resulted by suffocation of the airway due to hardening of secretions. Another problem is clogging caused by condensed water accumulated in the HME.

In order to solve the above problems, it is required to store larger amount of water in an expiratory gas and release the stored water into an aspiratory gas. The amount of water to be stored in the HME is preferably 44 mg/l, a saturated vapor amount in the air of 37° C. of a normal body temperature. It is very important that in aspiration (inhalation), the aspired gas is required to be near at the patient body temperature, as well as to keep high recovery of the absolute humidity. In storing and releasing of the above-mentioned amount of water, the thermal storage capability of the HMEs has to be improved for maintaining the required temperature.

In order to achieve the same purpose, HMEs with a thermal storage unit made of metal or the like, have been proposed. However, those metal type HMEs have several problems such as its bulkiness and heavy weight, and necessity of cleaning every time secretions stick thereto. Thus, the disposable HMEs, being small, light-weight, and inexpensive, have become in use.

On the other hand, it is not always preferable that the higher thermal storing effect is equipped with HMEs. For example, in the case that a humid expiratory gas of 37° C. enters into an anesthesia circuit via an HME from a patient in an operating room, condensation in the circuit is likely to occur because of large difference in temperature between the expiratory gas and typical room environment (23° C.).

Furthermore, if a dead cavity and/or a flow resistance are increased, there may occur a risk of increased burden on the patient required for breathing.

When anesthesia or artificial respiration is applied, the patient requires the aspiratory gas of 44 mg/l in absolute humidity, corresponding to relative humidity of 100% at a body temperature of 37° C. It is desired that the temperature of the aspiratory gas is adjusted closer to a body temperature for the required absolute humidity. If the temperature of the aspiratory gas is lower than the body temperature, the absolute humidity of 44 mg/l may not be achieved even if the humidity is increased.

In the meantime, in the preferable HMEs:
  an employed material and a manufacturing cost must be feasible in single-use;
  a thermal resistance must be provided such that the temperature of an expiratory gas becomes approximately 23° C. at the side of anesthesia circuit or the respiratory circuit;
  a thermal storage effect is required to regulate the temperature of the expiratory gas closer to the above temperature, 23° C., while avoiding increase in size, weight, dead cavity, flow resistance, and the like.

As an attempt of improving HMEs, a heat and moisture exchanging device provided with an auxiliary moisture and heat storage unit is proposed in Japanese Patent Application Laid-open Publication No. 2006-136461.

Further, as a modification of HMEs, in Japanese Patent Application Laid-open Publication No. 2000-225205, a mask that not only provides an improved humidifying function using a water-absorbing and water-retaining material but which also actively heats using a heat generator, thus adding heat and moisture, is proposed as a humidifying mask. In addition, a mask having a woven copper cloth for storing heat in an exhaled breath and adding the stored heat to an inhaled breath to warm the same in U.S. Pat. No. 5,706,802 and No. 6,196,221.

These heat and moisture exchanging devices do not have such functions as raising the temperature of the air to be inhaled and moisture absorption and release capabilities. In the existing heat and moisture exchanging devices, addition of a heater is required to achieve active heating function. Furthermore, in the above-mentioned masks, although heating of a gas to be inhaled is enabled, lack of moisture absorption and release capabilities may result in condense of water inside the mask.

SUMMARY

An object of the present invention is to provide a heat and moisture exchanger capable of appropriately adjusting the temperature and moisture of a gas such as air for a patient to inhale.

To accomplish the above and other objects, one aspect of the present invention is a heat and moisture exchanging device configured to be located between a respiratory system of a patient and an anesthesia circuit connected to an anesthesia apparatus, or a respiratory circuit connected to a respirator for maintaining a temperature and humidity of an aspired gas required to a patient under anesthesia or artificial respiration, comprising a heat storage carrier material, and a moisture absorption and release material added to the heat storage carrier material, at least one of density of the heat storage carrier material, number of cells of the heat storage carrier material, and an added amount of the moisture absorption and release material in the heat storage carrier material being set to decrease from the patient side to the side of the anesthesia apparatus or the respirator, along a flow direction of a respiratory gas in the heat storage carrier material.

The heat storage carrier material may include polyurethane and/or cellulose.

A density of the heat storage carrier material may be in the range of 20-80 kg/m$^3$. The density of the heat storage carrier material at the patient side may be adjusted ½-⅔ of that at the side of the anesthesia apparatus or the respirator. The number of cells of the heat storage carrier material may be in the range of 5-80 cells per inch.

The heat storage carrier material may carry at least one of calcium chloride, calcium carbonate, and calcium sulfate.

Another aspect of the present invention provides a respiratory heat and moisture exchanger for adjusting temperature and moisture of gas to be inhaled and having a heat storage carrier material and a moisture absorption and release material, wherein a value for at least one property selected from the properties of density, surface area, perforation rate, and number of cells of the heat storage carrier material that constitutes the respiratory heat and moisture exchanger is given a gradient along a direction of flow of respiration gas passing through the respiratory heat and moisture exchanger, such that the density is set to increase and the surface area, the perforation rate, or the number of cells is set to decrease on a downstream side of a flow of gas to be inhaled.

Yet another aspect of the present invention provides a respiratory heat and moisture exchanger for adjusting temperature and moisture of gas to be inhaled and having a heat storage carrier material and a moisture absorption and release material, wherein a value for at least one of a property selected from the properties of additive density and moisture absorption and release capability of the moisture absorption and release material added to the heat storage carrier material that constitutes the respiratory heat and moisture exchanger is given a gradient along a direction of flow of respiration gas passing through the respiratory heat and moisture exchanger, such that the additive density or the moisture absorption capability is set to increase, or the moisture release capability is set to decrease, on an upstream side of a flow of gas to be inhaled.

Further aspect of the present invention is a heat and moisture exchanging device in which any of the above respiratory heat and moisture exchanger is installed.

Yet further aspect of the present invention is a mask with a respiratory heat and moisture exchanging function, comprising a mask body provided at the mouth of a user, and a pair of ear hooks extending from two opposed outer lateral sides of the mask body, wherein the mask body having a respiratory heat and moisture exchanger including a heat storage carrier material carrying a moisture absorption and release material so that gas inhaled and exhaled by the user flows through the respiratory heat and moisture exchanger.

DETAILED DESCRIPTION

The present invention will be described in detail below in accordance with the embodiments of the present invention.

Embodiment 1

Figure 1:
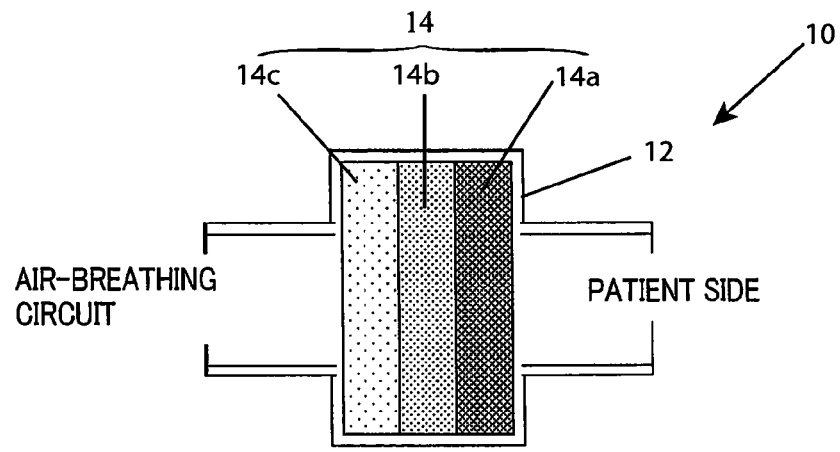
FIG. 1 shows a cross-sectional view of the three-staged HME according to one embodiment of the present invention.
Figure 2:
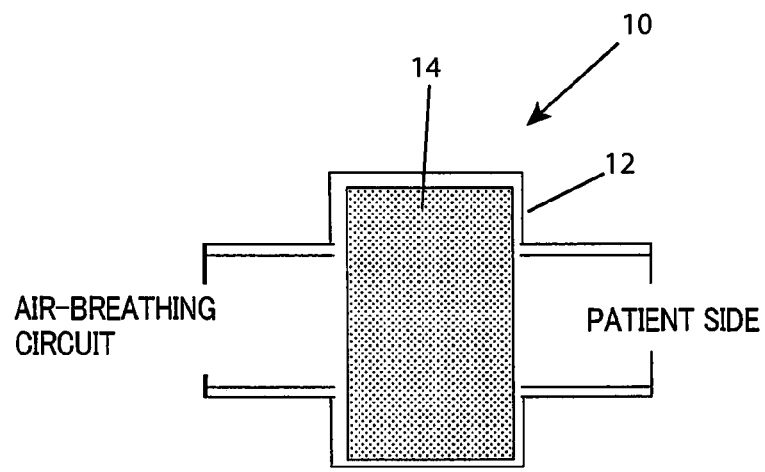
FIG. 2 shows a schematic cross-section of a conventional single-staged HME.
Figure 6:
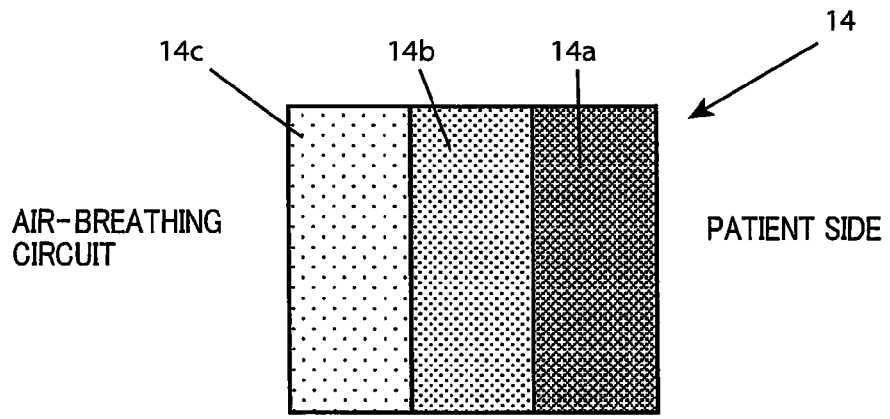
FIG. 6 shows a schematic view of a three-staged heat storage carrier material of the one embodiment of the present invention.

As shown in FIGS. 1 and 6, a three-staged HME 10 comprises a heat storage carrier material (thermal storage unit) 14 and a housing 12 containing the same. The heat storage carrier material 14 further includes three heat storage elements 14a-14c, each being made of polyurethane with a different density. Each element 14a-14c may include/consist of cellulose. The elements 14a-14c are arranged in series along a gas flow direction, as the density decreases from the patient side, so as to obtain a three-staged HME 10 according to one embodiment of the present invention. A density of each element 14a-14c is arranged 80, 57, and 30 kg/m$^3$ in descending order. To demonstrate its effectiveness, a test sample, a conventional single-staged HME 10 with a heat storage carrier material 14 of no density difference in FIG. 2 is evaluated for comparison of performance. The density of the heat storage carrier material 14 of the test sample amounts to 57 kg/m$^3$, an averaged density of the above three elements 14a-14c for the present embodiment. In addition, an artificial nose of commercial type, though not shown here, is also tested for comparison. The same housing of the same size is employed for both the present embodiment and test sample for containing the heat storage element(s). The heat storage carrier material 14 may be configured with combining four or more heat storage elements so that the elements each having a different density are laid on each other along the direction of a gas flow.

Figure 3:
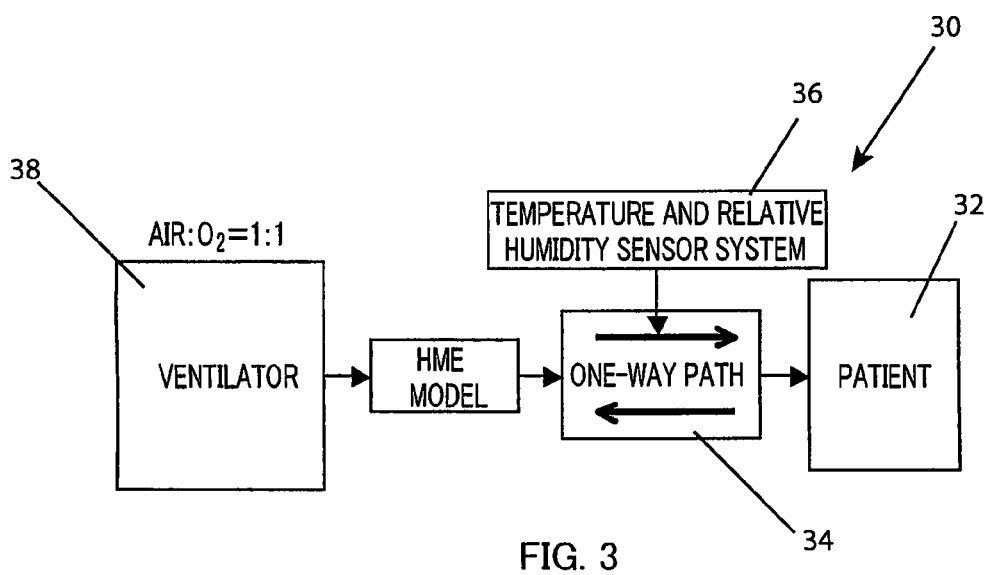
FIG. 3 is a schematic diagram of the experimental setup for evaluation of the HMEs.

FIG. 3 is a schematic diagram of the present experimental circuit 30. The measurements are made in a room-temperature range of 20 to 30° C., and 40 to 60% relative humidity. In the experimental circuit 30, the HME 10 of the present embodiment and the test sample are positioned between a mouth of a patient (actually a participant of the test) 32 and a ventilator 38 via a breathing-flow separator 34. In the experiments, a ventilator 38 (Type e500, Newport Medical Instruments, Inc.) is employed to provide an air-breathing volume of 600 ml with a respiration rate of 15 cycles/min for the participant, where a time ratio of expiration and aspiration is two. A sensor system 36 for recording temperature and relative humidity ("MOISCOPE™" manufactured by S.K.I.Net, Inc.), is used to measure temperature and moisture of the aspiration gas in a breathing-flow separator 34. The measured results are shown in FIGS. 4 and 5.

Figure 4:
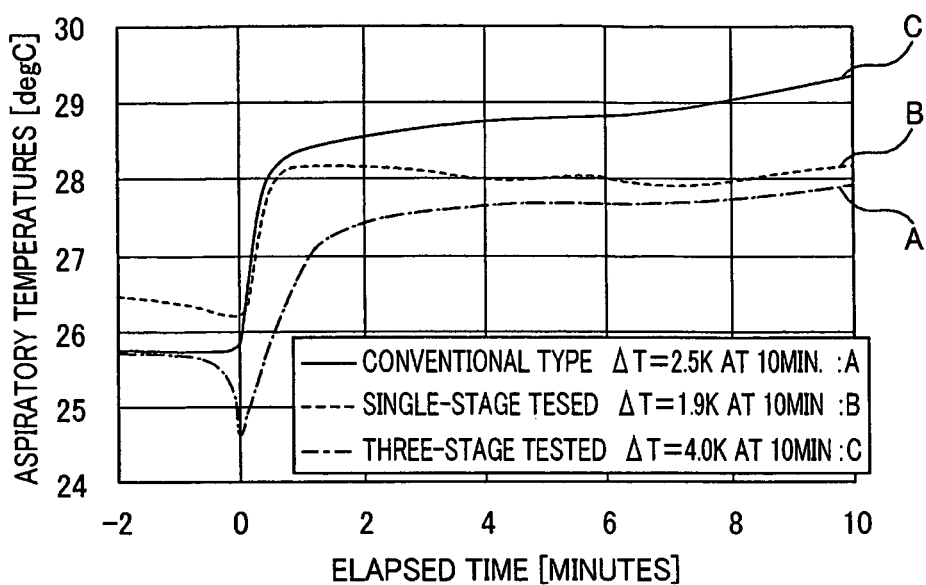
FIG. 4 compares variations in aspiratory temperature of the HMEs tested.
Figure 5:
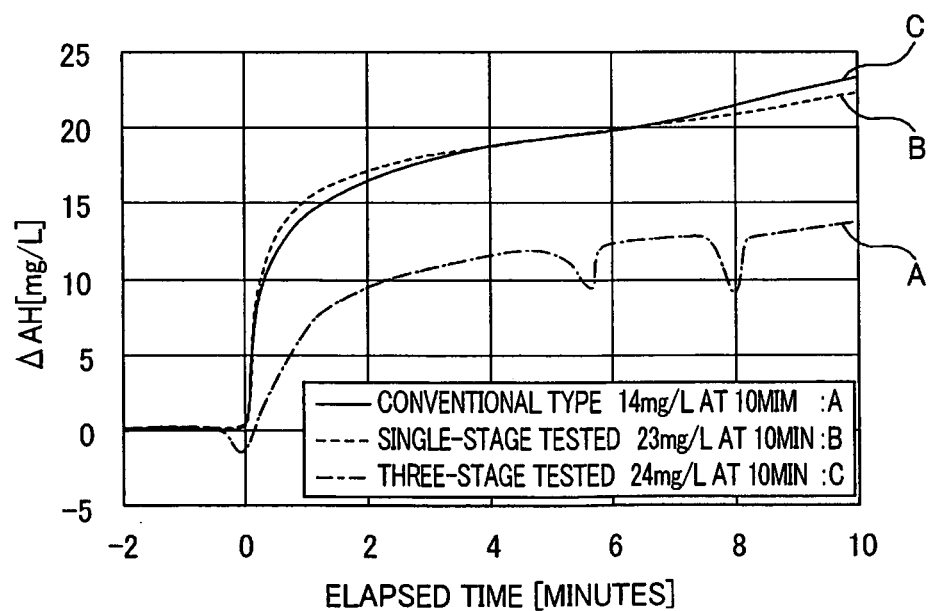
FIG. 5 is a graph showing variation of absolute humidity of aspiratory gas of tested HMEs.

Referring to FIG. 4, 10 minutes after start of the measurement, the HME of the present embodiment indicates a temperature increase ($\Delta T$), as labeled "C", of approximately 4.0K whereas the single-staged test sample without density difference, as labeled "B" shows approximately 1.9K. At the same time, it is also demonstrated the temperature increase effect is improved as compared to the conventional commercial product, as labeled "A". As shown in FIG. 5, it is appreciated the absolute humidity as labeled "C" is more increased than the conventional product.

Figure 7:
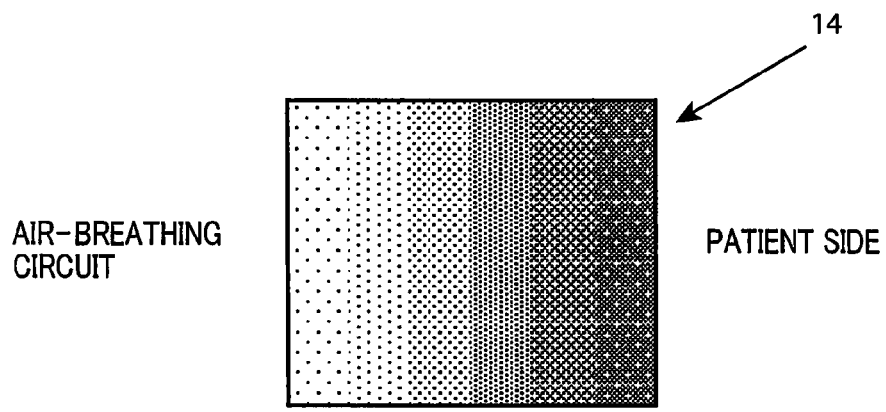
FIG. 7 shows a schematic view of a single-staged heat storage carrier material with a gradient structure according to a modification of the embodiment of the present invention.

In addition to the density of the heat storage carrier material, difference in a number of cells of the heat storage carrier material and/or an added amount of the moisture absorption and release material (heat and humidity regenerating material) in the heat storage carrier material contribute to improvement in performance of warming and humidifying. The "number of cells" is defined herein as a number of cells observed along a length of one inch on a cross-sectional surface of a material such as polyurethane. Furthermore, as shown in FIG. 7, providing a gradient in at least one physical property among density of the heat storage carrier material 14, number of cells of the heat storage carrier material 14, and an added amount of the moisture absorption and release material in the heat storage carrier material in a single heat storage carrier material 14, i.e., a gradient structure in the single heat storage carrier material 14, results in improvement of warming and humidifying characteristics. In this configuration, the physical property is set larger at the side closer to a patient.

Figure 8:
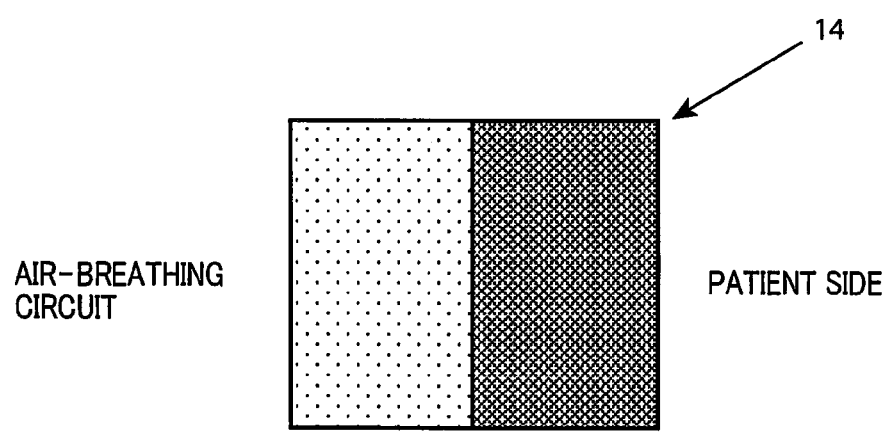
FIG. 8 shows a schematic view of a two-staged heat storage carrier material according to another modification of the embodiment of the present invention.
Figure 9:
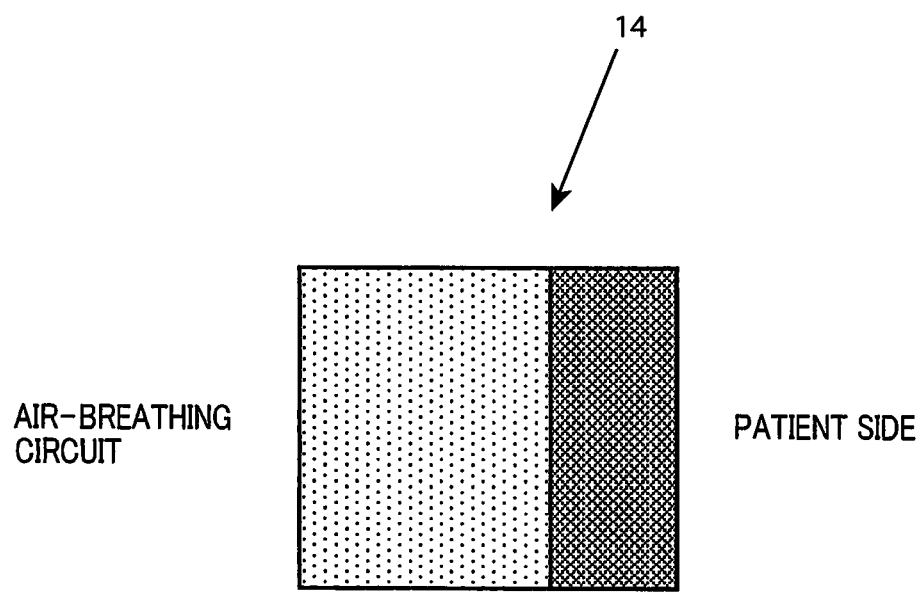
FIG. 9 shows a schematic view of a heat storage carrier material with a density gradient according to yet another modification of the embodiment of the present invention.

As shown in FIGS. 8 and 9, providing two heat storage elements 14a, 14c each having difference in at least one physical property among density of the heat storage carrier material 14, number of cells of the heat storage carrier material 14, and an added amount of the moisture absorption and release material in the heat storage carrier material 14 in an HME also results in improvement in warming/humidifying characteristics. In this configuration, the physical property is set larger at the side closer to a patient.

Hereinafter, a preferable numerical range of the physical properties are discussed. Regarding the density, if the largest value exceeds 80 kg/m$^3$, a patient will experience difficulty in respiration due to an increased flow resistance of the HME. If the smallest value is below 20 kg/m$^3$, shortage of heat capacity will decrease a heat storage effect, thus unpreferable increase in size is required. Consequently, the density is preferably in the range of 20-80 kg/m$^3$. For the same reasoning, the number of cells is preferably in the range of 5-80 cells per inch.

Moreover, in the difference in the density of the heat storage carrier material from the patients side to the anesthesia/respiratory circuit, in order to achieve optimal balance between the heat storage effect and the flow resistance, the ratio of the density at the patient side and that of the anesthesia/respiratory circuit side is preferably set half to two-thirds.

As described above, in the heat and moisture exchanging device according to the embodiment, a heat storing capacity can be larger at the parts where at least one of density of the heat storage carrier material, number of cells of the heat storage carrier material, and an added amount of the moisture absorption and release material in the heat storage carrier material is set larger, i.e., at the side closer to the patient. In the meantime, condensation in the anesthesia circuit or the respiratory circuit can be prevented by decreasing the flow resistance and gradual lowering of the gas temperature at the parts where at least one of density of the heat storage carrier material, number of cells of the heat storage carrier material, and an added amount of the moisture absorption and release material in the heat storage carrier material is set smaller, i.e., at the side closer to the anesthesia/respiratory circuit.

Embodiment 2

A description is given below of aspects of the present invention according to another embodiment. As an application of the respiratory heat and moisture exchanger, the description proceeds using as an example a heat and moisture exchanging device and a mask.

As described above, when regenerating heat from exhaled air into the air to be inhaled by a patient that is sent from an artificial respirator or an anesthetic device to the patient through a heat and moisture exchanging device, further increasing the heat regeneration rate of the respiratory heat and moisture regenerator disposed within the heat and moisture exchanging device is a problem to be solved.

In addition, with respect to the heat and moisture exchanging device described above, it is recognized that, as the capacity to add heat improves, there is room for improvement also in the capacity to add moisture. Further, with the structure proposed above, it has been confirmed that there is an unevenness in the amount of moisture stored in the moisture absorption and release material added to the respiratory heat and moisture exchanger inside the heat and moisture exchanging device.

More specifically, compared to on the circuit side of the heat and moisture exchanging device, where moisture is released, on the patient side the amount of moisture that is stored remains particularly large, thereby possibly causing clogging of the heat and moisture exchanging device due to localized increases in moisture inside the respiratory heat and moisture exchanger.

When the patient inhales, as the air or gas travels from the circuit side to the patient side in the heat and moisture exchanging device, moisture is released into the air to be inhaled, which contains little moisture and is dry (having a temperature of 23° C. and a humidity of 5% or less). As a result, the relative humidity on the patient side of the heat and moisture exchanging device increases while the relative humidity on the circuit side decreases, so that, in the same moisture absorption and release material, there is likely to appear an unevenness in distribution of the amount of moisture that is released.

For example, in a case in which calcium chloride ($CaCl_2$) is used as the moisture absorption and release material, in a case in which the relative humidity is 20% and in a case in which the relative humidity is 80%, in the case in which the relative humidity is 80% the rate of moisture release decreases, and therefore, on the patient side, where the moisture of the air to be inhaled has increased, the rate of moisture release decreases and the amount of moisture stored within the respiratory heat and moisture exchanger becomes excessive.

Accordingly, in the respiratory heat and moisture exchanger inside the heat and moisture exchanging device, limiting the imbalance in the amount of moisture accumulated on the patient side and on the circuit side, suppressing localized increases in moisture, and preventing clogging are problems to be solved.

Heat and Moisture Exchanging Device
Measuring Device

Figure 10:
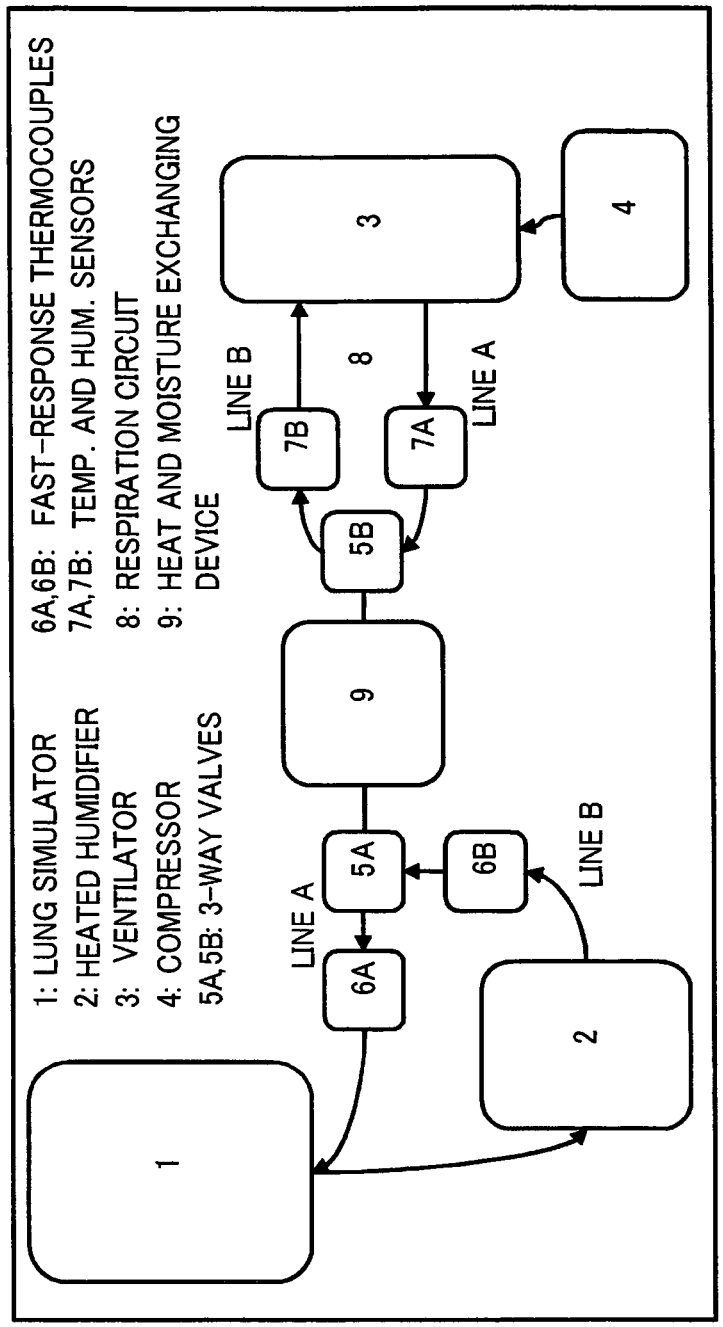
FIG. 10 is a schematic structural diagram of a measuring device used to confirm the effects of a respiratory heat and moisture exchanger according to another embodiment of the present invention.

The effect that the heat and moisture exchanging device provided with the respiratory heat and moisture exchanger according to the present embodiment has been confirmed experimentally by a measuring device configured using a lung simulator. A schematic structural diagram of the measuring device is shown in FIG. 10.

The measuring device simulates a patient's breathing, and is constituted by a lung simulator 1, a heated humidifier 2, a ventilator 3, a compressor 4, 3-way valves 5A and 5B, fast-response thermocouples 6A and 6B, temperature and humidity sensors 7A and 7B, and a respiration circuit 8.

The lung simulator 1 is a device that simulates the breathing movement of a patient. Two sets of lines are led out from the lung simulator 1, line A as an inhalation air line and line B as an exhalation air line. The inhalation line A is connected to a first port of the 3-way valve 5A through the fast-response thermocouple 6A that measures the temperature of the air that is inhaled. The exhalation line B is connected to the fast-response thermocouple 6B through the heated humidifier 2, and is further connected to a second port of the 3-way valve 5A.

To a third port of the 3-way valve 5A is connected a heat and moisture exchanging device (artificial nose) 9, which in turn is connected to the other 3-way valve 5B.

Two sets of lines are also led out from the ventilator 3 connected to the compressor 4, line A as an inhalation air line and line B as an exhalation air line. The inhalation air line A is connected to a first port of the 3-way valve 5B through the temperature and humidity sensor 7A that measures the temperature and humidity of the air that is inhaled. The exhalation air line B is connected to the temperature and humidity sensor 7B and further to a second port of the 3-way valve 5B.

The 3-way valves 5A and 5B switch between the inhalation air line A and the exhalation air line B in synchronism with the simulated breathing movement of the ventilator 3.

The exhaled air expelled from the lung simulator 1 is heated to 37° C. and humidified to 100% humidity by passing through the heated humidifier 2 and the heat and moisture contained therein is expelled to the heat and moisture exchanging device 9, thereby simulating the patient's respiratory function.

Ambient environment conditions were set to a temperature of 23° C.±1° C. and a relative humidity of 50%±20%.

Sample 1 consisted of a heat storage carrier material that constitutes the respiratory heat and moisture exchanger having a density or nominal density that was uniform, and Sample 2 consisted of a heat storage carrier material whose density or nominal density was given a density gradient, such that the density was lesser on the patient side and greater on the circuit side.

Each sample used a polyurethane foam to which calcium chloride was added. A nominal volume formed into a substantially cylindrical shape was within a range of 65 $cm^3$-200 $cm^3$, with the added amount of the calcium chloride within a range of 0.3-1.5 g.

Figure 11:
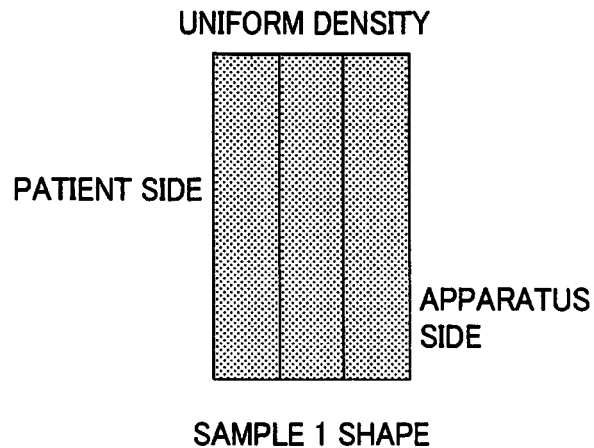
FIG. 11 is a comparative example (Sample 1) of a heat and moisture exchanger.
Figure 12:
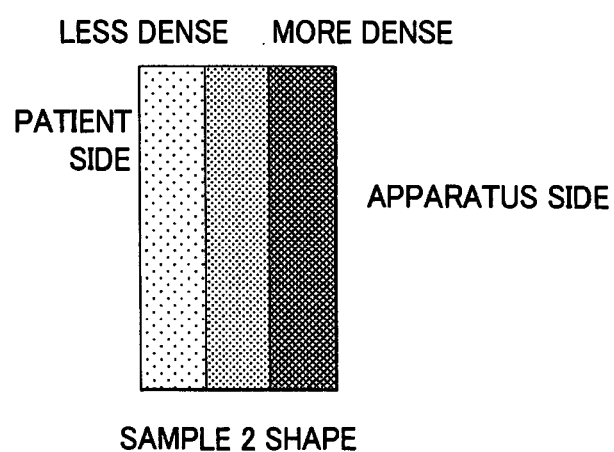
FIG. 12 is a schematic cross-sectional view of one example (Sample 2) of a heat and moisture exchanger according to Example 1 of the present invention.

The shape of Sample 1 is one in which the density of the polyurethane foam is made uniform as shown in FIG. 11. The density is 55 kg/$m^3$. The shape of Sample 2 is one in which the density of the polyurethane foam is given a gradient as shown in FIG. 12. The density ranges, in order from the patient side, from 30 to 55 to 70 kg/$m^3$.

Figure 13:
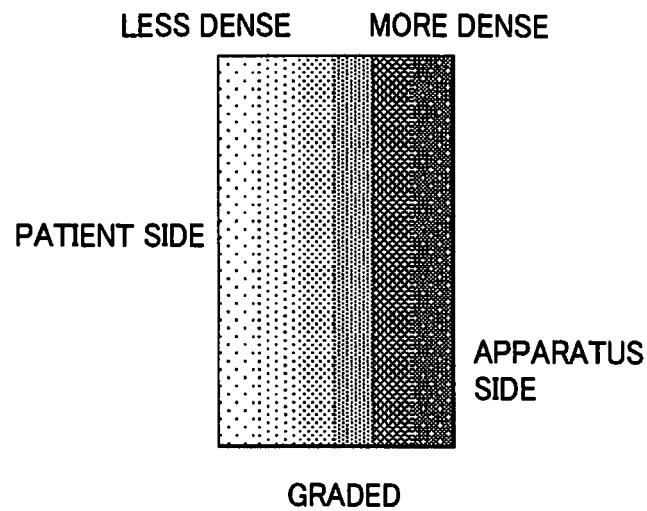
FIG. 13 is a schematic cross-sectional view of another example (Graded) of a heat and moisture exchanger according to Example 1 of the present invention.
Figure 14:
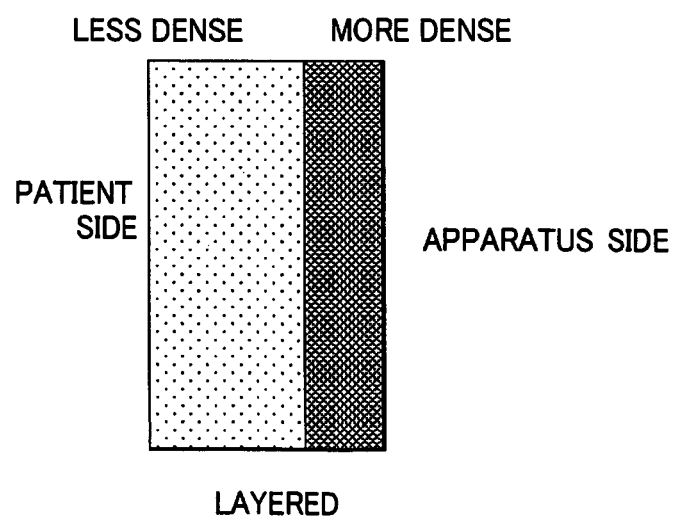
FIG. 14 is a schematic cross-sectional view of another and further example (Layered) of a heat and moisture exchanger according to Example 1 of the present invention.

As for the rest of the structure, with respect to the density or the nominal density of the heat storage carrier material, the density gradient, in which the density is greatest on the respiratory circuit and the anesthetic circuit side and least on the patient side, an arrangement may be adopted in which the density is slanted so that the density of each layer is changed in steps as shown in FIG. 13, or in which the density is layered so as to vary the thicknesses of the respective portions of different densities as shown in FIG. 14. Here, the surface area, the perforation rate, or the number of cells of the heat storage carrier material may be set relatively smaller at the patient side of the heat and moisture exchanging device.

Figure 15:
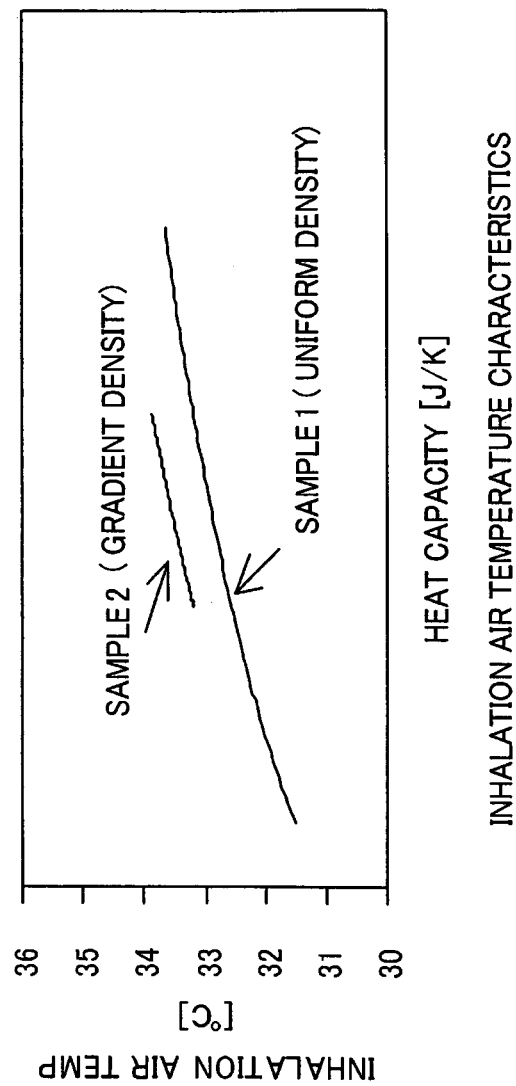
FIG. 15 is a diagram showing inhalation air temperature characteristics of a heat and moisture exchanger according to Example 1 of the present invention (Sample 2) and the comparative example (Sample 1)

When Sample 1 and Sample 2 are compared as shown in FIG. 15, even when the heat capacities of the samples are changed, in a case in which the heat capacity is the same the temperature of the air to be inhaled is higher in Sample 2.

From this, with respect to the density or the nominal density of the heat storage carrier material in the heat and moisture exchanging device, it can be confirmed that the efficiency with which the heat of the exhaled air is regenerated into the air to be inhaled that is sent to the patient from the artificial respirator or the anesthetic device through the heat and moisture exchanging device is improved by giving the density a gradient such that the density is greatest on the circuit side and least on the patient side.

Example 2

Next, two types of samples, Sample A and Sample B, were prepared in order to compare the heating and humidifying characteristics of a heat and moisture exchanging device provided with a respiratory heat and moisture exchanger according to a second embodiment of the present invention.
Sample A Using a heat storage carrier material made of polyurethane foam formed into a substantially cylindrical shape having a nominal volume of 52.3 cm$^3$, the carrier is divided into four layers, a first layer through a fourth layer, in which the density varies, in order from the patient side, from 30 to 55 to 55 to 70 kg/m$^3$, with each layer having a thickness of 5.5 mm. In other words, the heat storage carrier material of Sample A is given a density gradient such that the density increases from the patient side toward the circuit side. The heat storage carrier material is held inside a container provided with openings at two places through which simulated respiratory air passes, and connected to the measuring device through that container. The same arrangement applies for Sample B as well.

Figure 16:
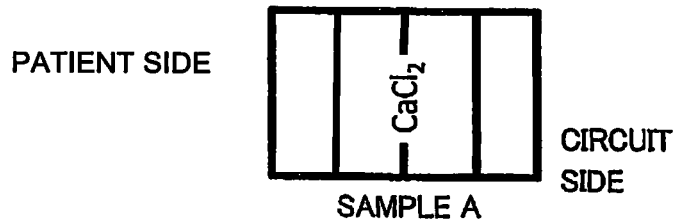
FIG. 16 is a schematic cross-sectional view of a heat and moisture exchanger according to the comparative example (Sample A) of the present invention.
Figure 17:
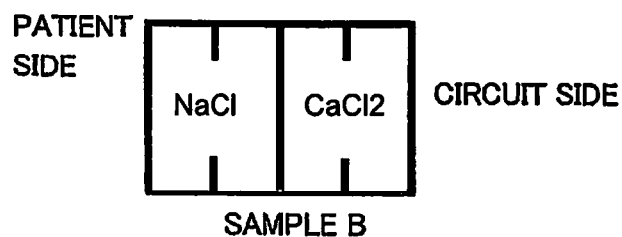
FIG. 17 is a schematic cross-sectional view of one example of a heat and moisture exchanger according to Example 2 (Sample B) of the present invention.

Calcium chloride is added to each of the layers of this heat storage carrier material, in amounts ranging, in order from the patient side, from 0.53 to 0.42 to 0.42 to 0.5 g. A schematic side view of Sample A is shown in FIG. 16.
Sample B In Sample B, sodium chloride is added to heat storage carrier material having the same density gradient as that of Sample A in amounts ranging, from the patient side, from 0 for the first layer, to 1.04 g for the second layer. As in Sample A, calcium chloride of 0.42 g is added to the third layer, and 0.5 g to the 4th layer. A schematic side view of Sample B is shown in FIG. 17.

An amount of water loss for each sample was measured using the measuring device described above and the measurement results compared.

The amount of residual water remaining inside each of the samples using the heat and moisture exchanging devices according to Samples A and B described above was evaluated through measuring an integrated value of the water amount in the exhaled breath from each sample and the residual water amount remained in each sample, and based on the total amount of the both calculating the water loss amount under simulated breathing conditions of 500 ml of displaced air per breath and 15 breaths per minute for 20 minutes continuously. Results of measurements of the amount of residual water in each layer of polyurethane foam are shown in FIG. 20, with results of a comparison of water loss amount for each sample, shown in FIG. 21.

Figure 20:
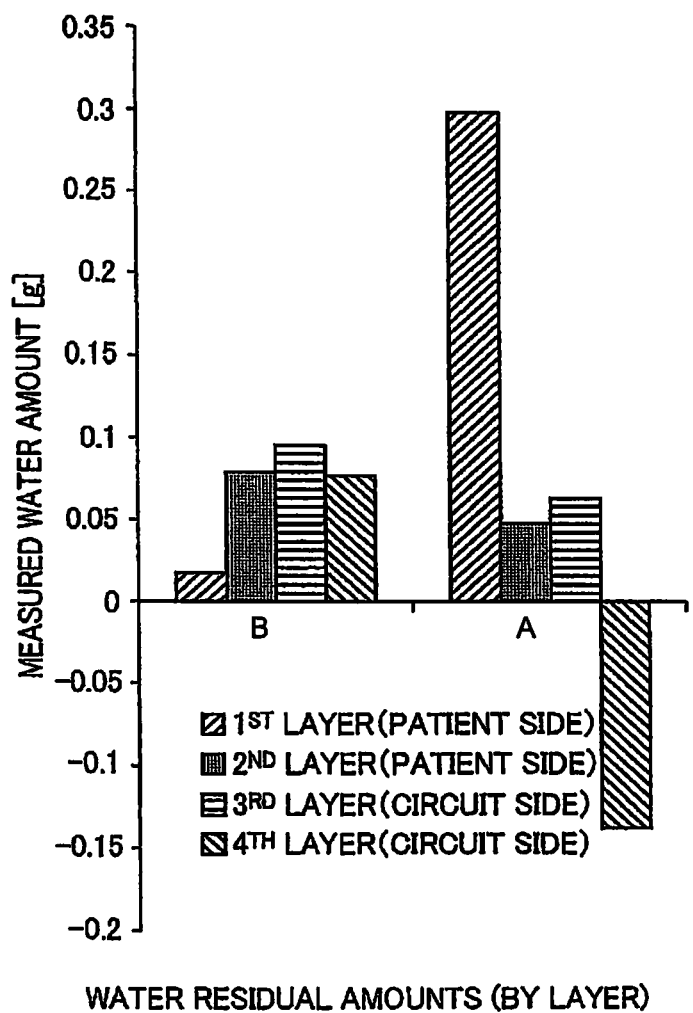
FIG. 20 is a diagram showing residual water amounts of a heat moisture exchanger according to Example 2 (Sample B) of the present invention and a comparative example (Sample A)

As for the amount of residual water in each layer of the heat storage carrier material shown in FIG. 20, in Sample A, to which calcium chloride alone was added, localized accumulation of water is particularly acute and the first layer of the patient side. However, in Sample B to which was added sodium chloride in place of calcium chloride, water accumulation is more or less uniform, indicating that localized increases of water have been prevented.

Figure 21:
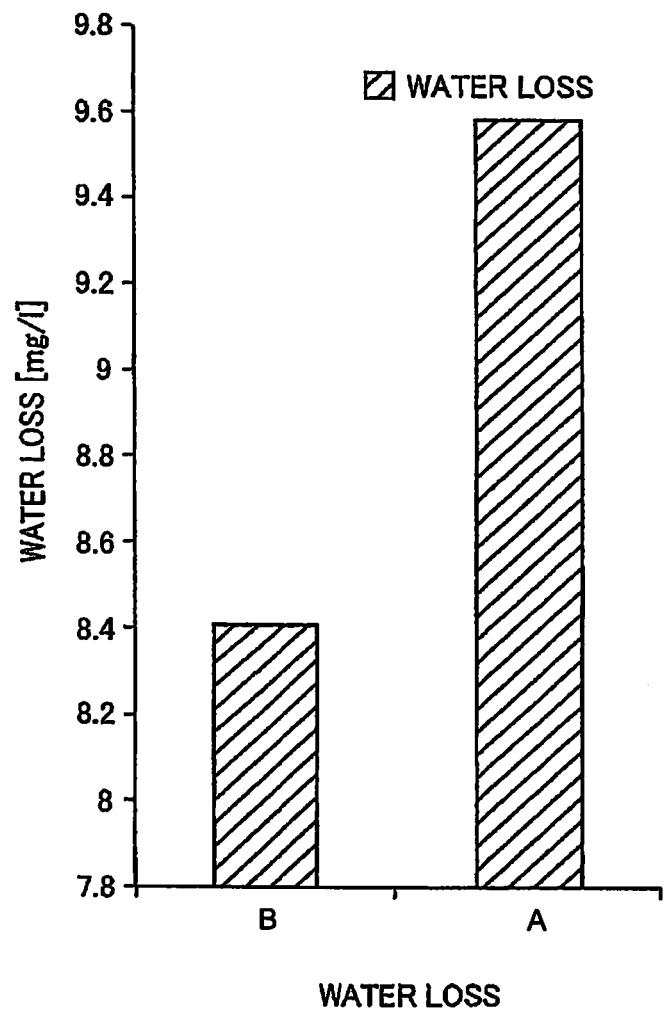
FIG. 21 is a diagram showing water loss in a heat and moisture exchanger according to Example 2 (Sample B) of the present invention and the comparative example (Sample A)

In addition, with respect to the water loss shown in FIG. 21, such water loss is less for Sample B, which employed sodium chloride as an additive, thus confirming that overall moisture release characteristics have been improved as well.

From these facts, it can be confirmed that a heat and moisture exchanging device having a structure in which sodium chloride is used on the patient side and calcium chloride is used on the circuit side can not only prevent the localized accumulation of moisture internally and prevent clogging but can also improve moisture release efficiency.

Figure 18:
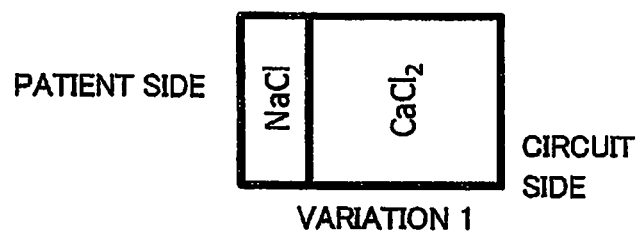
FIG. 18 is a schematic cross-sectional view of another example (Variation 1) of a heat and moisture exchanger according to Example 2 of the present invention.
Figure 19:
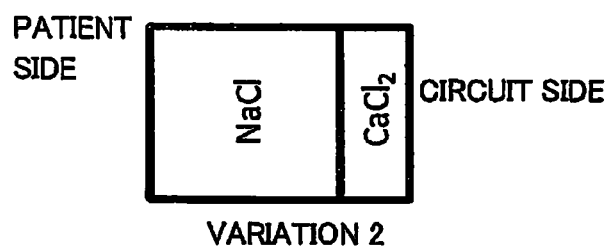
FIG. 19 is a schematic cross-sectional view of another and further example (Variation 2) of a heat and moisture exchanger according to Example 2 of the present invention.

It is to be noted that, as configurations other than those illustrated in Samples A and B, so long as sodium chloride is provided on the patient side the thickness of the heat storage carrier material provided with calcium chloride and sodium chloride can be varied as shown in FIG. 18 or FIG. 19.

Moreover, as the moisture absorption and release material a combination of sodium chloride and calcium chloride may be used, in which the relative proportions of two chemicals are varied depending on the position of the heat storage carrier material. The relative proportions should be such that there is more sodium chloride on the patient side and more calcium chloride on the circuit side.

Finally, a description is given of the effect of the present embodiment. Comparing the moisture absorption and release characteristics of sodium chloride and calcium chloride, it can be seen that calcium chloride has the greater moisture absorption capability and absorbs more moisture than the sodium chloride does. By contrast, sodium chloride which releases moisture when the relative humidity is 75% or less, has greater moisture release capabilities than calcium chloride does, which continues to absorb moisture even when the relative humidity is 50%.

Utilizing these differences in moisture absorption and release between sodium chloride and calcium chloride, and providing a carrier on the patient side with sodium chloride which has not been used at all as a moisture absorption and release material for conventional heat and moisture exchanging devices, makes it possible to improve the moisture release capabilities at that portion and to prevent clogging due to water accumulation.

Example 3

Masks

Figure 22A:
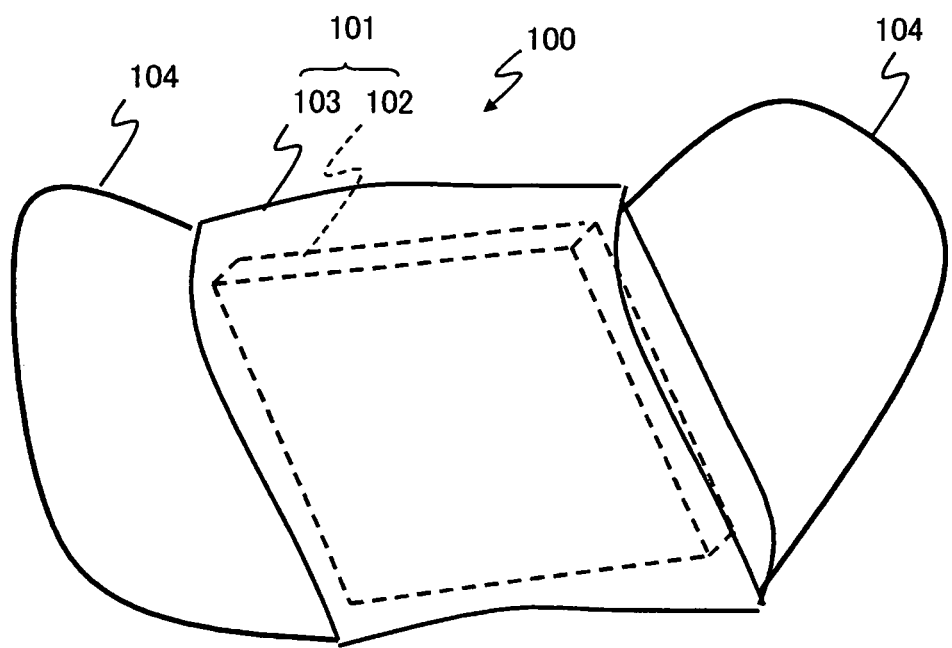
FIG. 22A is a schematic view of a mask of one example according to Example 3 of the present invention.
Figure 22B:
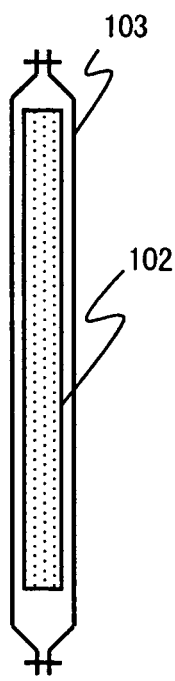
FIG. 22B is a schematic cross-sectional view of a mask body of one example according to Example 3 of the present invention.

Here, a mask according to one embodiment of the present invention will be described with reference to FIGS. 22A and 22B. FIG. 22A shows a schematic view of an exemplary mask according to Example 3 of the present invention. FIG. 22B shows a schematic cross-sectional view of the mask body 101 in FIG. 22A.

A mask 100 of the present embodiment includes a mask body 101 to be placed adjacent a wearer's mouth or nasal apertures, the wearer's breath passing the mask body 101 in the direction of its thickness, and a pair of ear hooks 104 extending from each lateral side portion of the mask body 101 to be hung behind the wearer's ears. Each of the ear hooks 104 consists of an elastic cord member made of any suitable material.

The mask body 101 is a generally plane-shaped part, formed by encompassing a plate-like heat and moisture exchanger 102 with an exterior material 103 such as cotton cloth. The heat and moisture exchanger 102 is made up of for example a polyurethane foam as heat storage carrier material and calcium chloride as moisture absorption and releasing material carried in the polyurethane foam. The heat and moisture exchanger 102 is shaped into a rectangular plate having elasticity in general. When the heat and moisture exchanger 102 is formed with such material as can be directly applied to the wearer's mouth into an appropriate shape, it may not be necessary to provide the exterior material 103.

The heat and moisture exchanger 102 may be provided with an intermediate member to be applied to the skin around the wearer's mouth and nose on the surface thereof. According to this construction, the heat and moisture exchanger 102 does not directly touch the wearer's skin and the wearer feels more comfortable when wearing the mask 100. A coarse cotton cloth as gauze and other suitable material may be applied to the intermediate member. In option, the exterior material 103 may be also used as the intermediate member.

According to the above construction, heat in the exhaled breath is stored in the polyurethane foam as the heat storage carrier material and moisture in the exhaled breath is adsorbed or absorbed by calcium chloride as the moisture absorption and releasing material. Thus, both retaining of the heat in the exhaled breath and condensation inside the mask body 101 are prevented. Moreover, since the heat and the moisture captured from the exhaled breath are released into a gas to be inhaled when inhaling, an effect of warming and moistening of the gas can be achieved.

Further, if, as the moisture and heat exchanger 102, a respiratory heat and moisture exchanger in which a value for at least one property selected from the properties of density, surface area, perforation rate, and number of cells of the heat storage carrier material that constitutes the respiratory heat and moisture exchanger is given a gradient along a direction of flow of respiration air passing through the respiratory heat and moisture exchanger, such that the density is set to increase and the surface area, the perforation rate, or the number of cells is set to decrease, on a downstream side of a flow of air to be inhaled is employed, regeneration efficiency of the heat in the exhaled breath is improved as described above regarding the heat and moisture exchanging device.

Alternatively, if, as the moisture and heat exchanger 102, a respiratory heat and moisture exchanger having a heat storage carrier material and a moisture absorption and release material wherein a value for at least one of a property selected from the properties of additive density and moisture absorption and release capability of the moisture absorption and release material added to the heat storage carrier material that constitutes the respiratory heat and moisture exchanger is given a gradient along a direction of flow of respiration air passing through the respiratory heat and moisture exchanger, such that the additive density or the moisture absorption capability is set to increase, or the moisture release capability is set to decrease, on an upstream side of a flow of air to be inhaled, is employed, clogging due to water accumulation is prevented.

It is to be noted that although a combination of sodium chloride and calcium chloride, for example, can be used for the moisture absorption and release material, the present invention is not limited thereto. Provided the material is harmless and can be made to come into contact with respiratory gases, other and different combinations of compounds may be adopted for the moisture absorption and release material. Alternatively, a single compound such as calcium chloride may be adopted for the moisture absorption and release material.

With the above-described structure, the heat storage unit, in which the carrier material of the respiratory heat and moisture exchanger is densest, is located upstream when the patient inhales, thereby enabling heat loss due to radiation and the like to be reduced and improving the efficiency with which the heat of the exhaled gas is regenerated.

Further, heat of adsorption or heat of absorption generated when moisture is adsorbed or absorbed can be stored in the dense heat storage unit which is located downstream when the patient exhales, thus improving the efficiency with which the heat of the exhaled gas is regenerated.

Moreover, on the upstream end of the flow of gas to be inhaled of the respiratory heat and moisture exchanger, the density or the moisture absorption capacity is enhanced, or the moisture release capacity is reduced, thereby enabling clogging of the heat and moisture exchanger due to moisture accumulation on the patient side to be prevented.

It is to be noted that although the present invention is described in terms of embodiments thereof with reference to the accompanying drawings, the present invention is not limited to these embodiments. In addition, the present invention encompasses all variations and equivalents within the scope of the invention.

What is claimed is:

1. A heat and moisture exchanging device configured to be located between a respiratory system of a patient and an anesthesia circuit connected to an anesthesia apparatus, or a respiratory circuit connected to a respirator for maintaining a temperature and humidity of an inhaled gas required to a patient under anesthesia or artificial respiration, comprising:
    a heat storage carrier material; and
    a moisture absorption and release material added to the heat storage carrier material,
    at least one of density of the heat storage carrier material, number of cells of the heat storage carrier material, and an added amount of the moisture absorption and release material in the heat storage carrier material being set to decrease from the patient side to the side of the anesthesia apparatus or the respirator, along a flow direction of a respiratory gas in the heat storage carrier material.

2. The heat and moisture exchanging device claimed in claim 1, wherein the heat storage carrier material includes polyurethane and/or cellulose.

3. The heat and moisture exchanging device claimed in claim 2, wherein a density of the heat storage carrier material is in a range of 20 to 80 kg/m$^3$.

4. A heat and moisture exchanging device claimed in claim 3, wherein the density of the heat storage carrier material at the side of the anesthesia apparatus or the respirator is adjusted half to two-thirds of that at the patient side.

5. A heat and moisture exchanging device claimed in claim 2, wherein the number of cells of the heat storage carrier material is in the range of 5 to 80 cells per inch.

6. A heat and moisture exchanging device claimed in claim 2, wherein the heat storage carrier material carries at least one of calcium chloride, calcium carbonate, and calcium sulfate.

7. A heat and moisture exchanging device provided with the heat and moisture exchanger according to claim 1 inside a housing that has a first connecting portion to which is connected a tube communicating with a patient's air passage and a second connecting portion coupled to a source for supplying gas to be inhaled by the patient and a line for expelling gas exhaled by the patient.

8. The heat and moisture exchanging device according to claim 7, wherein the heat storage carrier material includes polyurethane having a density within a range of 1-150 kg/m$^3$.

9. The heat and moisture exchanging device according to claim 7, wherein the moisture absorption and release material includes calcium chloride and sodium chloride, and sodium chloride is added to the respiratory heat and moisture exchanging device on the first connecting portion side thereof and calcium chloride is added on the second connecting portion side thereof.

10. A respiratory heat and moisture exchanger for adjusting temperature and moisture of gas to be inhaled and having a heat storage carrier material and a moisture absorption and release material,
wherein a value for density of the heat storage carrier material that constitutes the respiratory heat and moisture exchanger is given a gradient along a direction of flow of respiration gas passing through the respiratory heat and moisture exchanger, such that the density is set to increase on a downstream side of a flow of gas to be inhaled.

11. The heat and moisture exchanger according to claim 10, wherein the moisture absorption and release material includes sodium chloride.

12. A mask with a respiratory heat and moisture exchanging function, comprising:
a mask body provided at the mouth of a user; and
a pair of ear hooks extending from two opposed outer lateral sides of the mask body,
wherein a respiratory heat and moisture exchanger for adjusting temperature and moisture of gas to be inhaled and having a heat storage carrier material and a moisture absorption and release material is disposed within the mask body,
wherein a density of the heat storage carrier material that constitutes the respiratory heat and moisture exchanger is given a gradient along a direction of flow of respiration gas passing through the respiratory heat and moisture exchanger, such that the density is set to increase on a downstream side of a flow of gas to be inhaled.

13. The mask according to claim 12, wherein the heat storage carrier material includes a polyurethane foam.

14. The mask according to claim 12, wherein the moisture absorption and release material includes calcium chloride or sodium chloride.

15. The mask according to claim 12, wherein a contact-preventing member is provided on a user side of the mask body so that the respiratory heat and moisture exchanger and the skin of the user do not come into contact with each other.

16. A respiratory heat and moisture exchanger for adjusting temperature and moisture of gas to be inhaled and having a heat storage carrier material and a moisture absorption and release material,
wherein a density of the heat storage carrier material is given a gradient along a direction of flow of respiration gas passing through the respiratory heat and moisture exchanger, such that density of the heat storage carrier material is set to increase on a downstream side of a flow of gas to be exhaled, the moisture absorption and release material being added to a part where the density of the heat storage carrier material is set larger, and wherein the moisture absorption and release material includes a sodium chloride.

17. A heat and moisture exchanger element comprising:
a heat storage carrier material; and
a moisture absorption and release material added to the heat storage carrier material,
wherein respective values for a density of the heat storage carrier material, moisture absorption capability and moisture release capability of the moisture absorption and release material added to the heat storage carrier material that constitutes the heat and moisture exchanger are given a gradient along a direction of flow of respiration gas passing through the heat and moisture exchanger element, and
wherein the moisture absorption and release material includes sodium chloride.

18. A heat and moisture exchanger element comprising:
a heat storage carrier material; and
a moisture absorption and release material added to the heat storage carrier material,
wherein the moisture absorption and release material includes calcium chloride and sodium chloride, and sodium chloride is added to one side thereof and calcium chloride is added to an opposite side thereof.

* * * * *